United States Patent [19]

Haber

[11] Patent Number: 5,067,490

[45] Date of Patent: * Nov. 26, 1991

[54] SINGLE USE, SAFETY BLOOD COLLECTING DEVICE

[75] Inventor: Terry M. Haber, El Toro, Calif.

[73] Assignee: Habley Medical Technology, Corp., Laguna Hills, Calif.

[*] Notice: The portion of the term of this patent subsequent to Jan. 9, 2007 has been disclaimed.

[21] Appl. No.: 366,009

[22] Filed: Jun. 14, 1989

Related U.S. Application Data

[63] Continuation of Ser. No. 141,019, Jan. 5, 1988, Pat. No. 4,892,107.

[51] Int. Cl.⁵ .................................................. A61B 5/00
[52] U.S. Cl. ..................................... 128/763; 604/110; 604/198
[58] Field of Search ............... 604/192, 193, 196, 198, 604/263, 232, 110; 128/763-765

[56] References Cited

U.S. PATENT DOCUMENTS

| | | | |
|---|---|---|---|
| 4,643,199 | 2/1987 | Jennings, Jr. et al. | 128/763 |
| 4,643,200 | 2/1987 | Jennings, Jr. | 604/198 |
| 4,655,751 | 4/1987 | Harbaugh | 604/198 |
| 4,693,708 | 9/1987 | Wanderer et al. | 604/198 |
| 4,702,738 | 10/1987 | Spencer | 604/263 |
| 4,738,663 | 4/1988 | Bogan | 604/198 |
| 4,752,290 | 6/1988 | Schramm | 604/198 |
| 4,758,231 | 7/1988 | Haber et al. | 128/763 |
| 4,774,964 | 10/1988 | Bonaldo | 128/763 |
| 4,790,827 | 12/1988 | Haber et al. | 128/763 |
| 4,813,426 | 3/1989 | Haber et al. | 128/763 |
| 4,826,491 | 5/1989 | Schramm | 604/198 |
| 4,834,717 | 5/1989 | Haber et al. | 604/232 |
| 4,840,185 | 6/1989 | Hernandez | 604/263 |
| 4,846,808 | 7/1989 | Haber et al. | 128/763 |
| 4,850,374 | 7/1989 | Diaz-Ramos | 604/198 |
| 4,871,355 | 10/1989 | Kikkawa | 128/763 |
| 4,892,107 | 1/1990 | Haber | 604/110 |
| 4,900,310 | 2/1990 | Ogle, II | 604/198 |

Primary Examiner—Stephen C. Pellegrino
Assistant Examiner—Ralph A. Lewis
Attorney, Agent, or Firm—Townsend and Townsend

[57] ABSTRACT

A shielded safety syringe comprising a cylindrical outer sleeve and an inner needle carrier holding a double-pointed needle in fluid communication with a vacuum tube and slidable within the outer sleeve between two positions. In the first position, the needle projects from the outer sleeve and is exposed for drawing blood. In the second position, the needle is retracted within the outer sleeve. The needle carrier is releasably held in the first position so that it can be readily moved into the second position after use. After the needle has been retracted into the sleeve the carrier is locked in its second position to prevent health care workers from coming into accidental contact with the used needle.

2 Claims, 1 Drawing Sheet

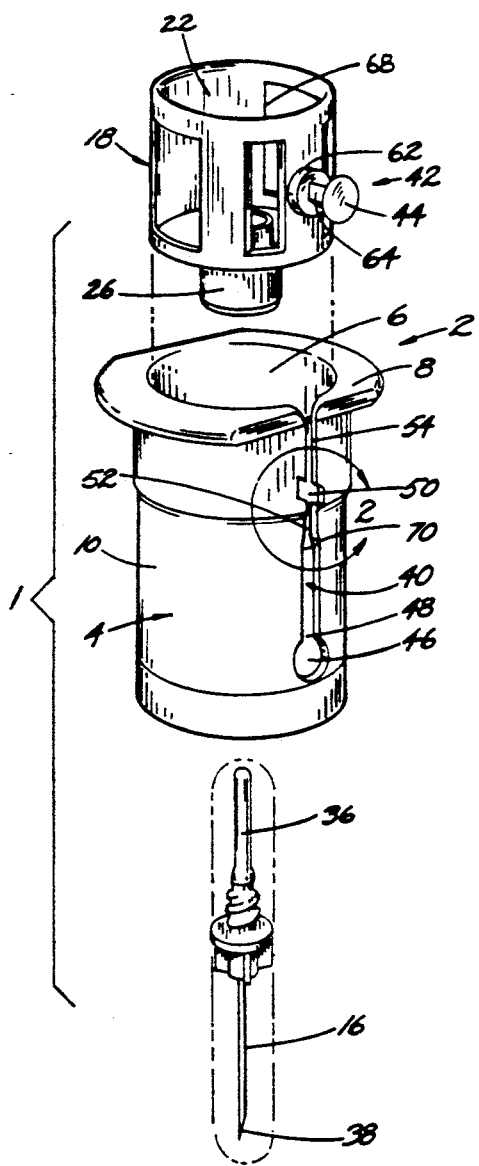
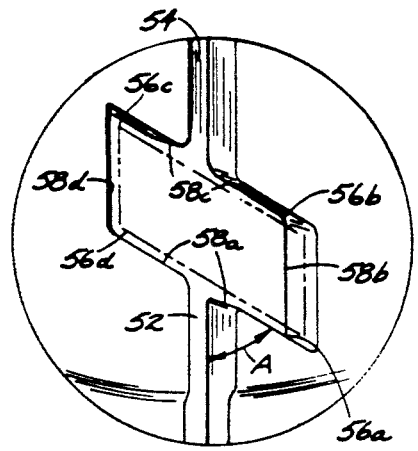
fig1
fig2
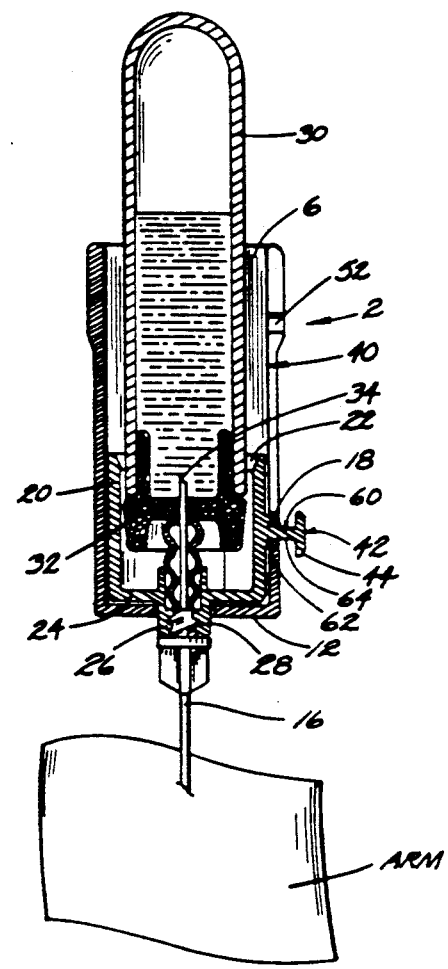
fig3
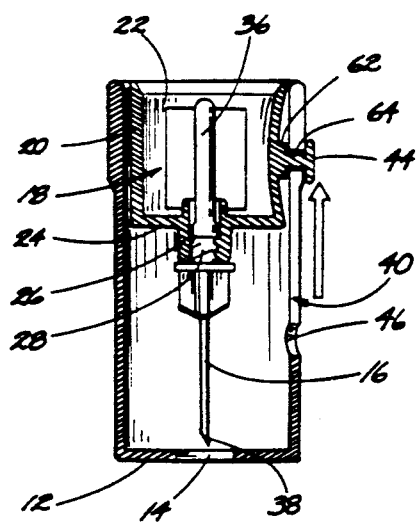
fig4

SINGLE USE, SAFETY BLOOD COLLECTING DEVICE

This is a continuation of application Ser. No. 141,019 filed Jan. 5, 1988, now U.S. Pat. No. 4,892,107.

BACKGROUND OF THE INVENTION

Although hypodermic syringes may be used for blood sample collection purposes vacuum tube phlebotomy, where one or more samples of a patient's blood are successively drawn into respective evacuated blood collection tubes by way of a double ended hypodermic needle has become the procedure of choice.

Typically, this is currently done with a needle having two sharp ends, mounting the needle in a generally cup-shaped holder, and placing a previously-evacuated collection tube into the holder so that the proximal end of the needle cannula pierces an elastomeric seal of the tube after the opposite needle end has been inserted into the patient's vein. As soon as the proximal needle cannula pierces the tube, the vacuum therein draws blood from the vein, through the needle, into the tube. When sufficient blood has been collected, the pre-evacuated tube is withdrawn from the needle cannula. Often, one or more additional evacuated tubes are inserted into the holder. After the desired number of samples have been drawn, the needle is withdrawn from the vein and discarded.

After use the needle must be disposed of, typically by first removing it from the blood collection tube holder, recapping it, and then inserting it into a Sharp's receptacle. To prevent the reuse of the needle it is sometimes broken. However, this has been found to cause aerosol contamination frequently. Health care workers are susceptible to accidental and potentially infectious needle strikes when they dispose of contaminated needle cannula after use. This can expose them to a communicable disease such as AIDS or hepatitis B. To avoid infections, health care workers are now instructed neither to recap contaminated needles nor to "manipulate contaminated needles by hand," but rather to dispose of them in Sharp's containers, molded plastic receptacles provided specifically for receiving waste which is potentially biologically hazardous, from blood precautionary patients.

Even these improved procedures do not fully protect the health care worker from accidental needle strike and the possibility of being accidentally exposed to a communicable disease as the act of inserting a contaminated cannula into the Sharp's container may itself result in accidental needle strike. The worker must still handle potentially contaminated needles because the cup-shaped holders for receiving the needles are typically reused, often as much as two hundred times, until the threads into which the needle is screwed become worn. In addition, the Sharp's containers are often not near enough to the location of use, causing the health care worker to carry the potentially contaminated needles to the disposal container. At other times, the health care worker may simply choose to dispose of the needle wherever and whenever most convenient, where an exposed and contaminated needle cannula in an unexpected location may pose yet a further health hazard.

The virtually unavoidable mini-accidents caused by accidental needle strikes have become a particularly serious concern since the spread of the AIDS disease, which has, in fact, been transmitted in this manner. Thus, a blood test for such diseases as AIDS and hepatitis B is now required whenever such an accident occurs. The necessary testing of health care workers who have received an inadvertent needle strike has thereby led to considerable additional costs.

Recently the assignee of the present invention has developed a safety blood collection tube holder, which is the subject of another, currently pending patent application. Briefly, such a safety holder has a needle/-vacuum tube carrier which is slidably disposed within a tubular sleeve. The carrier is freely movable between first and second positions in which the needle projects from the housing or is encapsulated within the housing so that it cannot be directly contacted by health care workers. The carrier cannot be returned to its first position therefore the used needle cannula is never again exposed. So long as a contaminated needle cannula is extended in an unshielded condition it poses a potential infection hazard.

SUMMARY OF THE INVENTION

The present invention provides a single use safety blood collection device, which permits retraction of the hypodermic needle after its use into the sleeve of the device, itself to thereby encapsulate the used needle so that the probability of sticking oneself with it is greatly reduced, or eliminated. Once the needle is retracted after use it cannot thereafter be extended again. Thus, the present invention substantially reduces the probability of spreading infectious diseases as a result of accidental needle strikes.

This is achieved, in accordance with the present invention, by adding a self-locking mechanism to the blood collection device which was the subject matter of the above referred to copending patent application. To this end, the syringe of the present invention has a needle carrier which is axially movable within an outer, tubular sleeve between first and second positions in which the needle is extended or retracted, respectively. The sleeve includes two axially spaced apart, radially oriented openings which cooperate with an actuator integral to said needle carrier and that radially projects from the carrier. When the actuator is in one or the other of the two openings, the carrier is in one of the two operating positions.

In the preferred embodiment of the invention, the sleeve has an open end and a closed end including an aperture through which the needle can be extended. The distal opening is adjacent to the closed end of the sleeve, the proximal opening is adjacent to the open end thereof, and a slot extends from the first opening to the second opening and onto the open end of the sleeve. This splits the sleeve longitudinally and permits the opening of the slot by applying corresponding opposing forces to the slot edges.

The slot has a width where it communicates with the distal opening which is greater than the width of the slot where it intersects the proximal opening. Moreover, the width of the slot at the distal and proximal openings is less than the corresponding transverse dimension of the openings and the width of the proximal opening is slightly less than the width of the slot at the distal opening.

The actuator is defined by a radially extending stem, an inner portion of which defines a base section attached to the needle carrier and dimensioned so that it can readily enter the distal opening. An intermediate portion of the stem adjoining the base section is shaped so that it fits into the proximal opening. Lastly, the actuator includes a head attached to the intermediate stem portion and located exteriorly of the sleeve so that a health care worker can manually engage the head with his or her thumb while holding the sleeve with the hand and longitudinally slide the head and therewith the carrier from the distal to the proximal opening as is described below.

The portion of the carrier which mounts the stem is resiliently constructed so that it biases the stem radially outwardly. When the stem is aligned with the distal opening this biasing force moves the base section of the stem into the distal opening and thereby securely holds the carrier in its first position.

To move the carrier from the distal (armed) to the proximal (safe) position, and thereby retract the needle into the sleeve, the health care worker presses the head radially inwardly opposing the biasing force of the carrier to disengage the head's base section from the distal opening and align the intermediate stem portion with the slot. Thereafter the head is retracted rearwardly, that is towards the proximal opening. Since the intermediate stem portion has a width less than the width of the slot at the distal opening it can readily enter the slot. As the slot narrows towards the proximal opening the continued distal-to-proximal movement of the head by the worker generates a component force which elastically deforms the sleeve and opens the slot so that the actuator can continue its movement towards the proximal opening. Once the intermediate stem portion is at the proximal opening, the resiliency of the sleeve automatically causes it to return to its original position, thereby closing the slot to its original width. Consequently, once the intermediate stem portion is in the proximal opening it confronts slot width which is less than the width of the intermediate portion. The actuator, the carrier and the needle are thereby effectively locked into their retracted position.

A particular advantage of the present invention is the fact that the alignment of the intermediate stem portion with the proximal secured opening, and the locking of the forces therein are automatic. It is therefore not necessary for the health care worker to tediously pre-align the actuator with the proximal opening to establish the lock. The movement path for the carrier prescribed by the slot is such that the actuator necessarily becomes aligned with the proximal opening in the course of retracting the used needle cannula into the housing. Once alignment has taken place, the resilient deflection of the sleeve as the carrier is moved towards the proximal opening is utilized to automatically lock the intermediate stem portion in the proximal opening by permitting the housing to snap back into its relaxed position. Since the base section and the head of the actuator have a larger cross section than the proximal secured opening, the actuator becomes immovable. Since the intermediate stem portion has a width greater than the adjoining slot the actuator and therewith the carrier and the needle are locked in place. Thus, the present invention effectively provides a self-activating snap lock for the carrier which is engaged automatically by virtue of proper positioning of the actuator in the proximal opening, coupled with the fact that the movement path for the carrier prescribed by the slot is such that the actuator necessarily becomes aligned with the proximal opening in the course of retracting the used needle cannula into the housing.

Thus, the present invention provides a single-use, safety blood collection holder which is preferable to the one which forms the subject matter of the above-mentioned copending application because it produces a safely disposable module of one-half the volume of said copending application. Moreover, the present invention is so simple that the worker handling it need not use two hands to lock the device into its safe disposal position. The locking of the carrier in the retracted position is a one-hand automatic operation and a necessary consequence of the retraction of the needle into the sleeve. Consequently, the present invention significantly enhances the safety of used blood drawing devices and thereby becomes an important instrument in the fight against the accidental or careless spread of dangerous infectious diseases such as AIDS or hepatitis B.

BRIEF DESCRIPTION OF THE DRAWINGS

FIG. 1 is an exploded view of the blood collection device of the present invention.

FIG. 2 is an enlarged view of the portion of the locking device of FIG. 1.

FIG. 3 is a cross-sectional view of the blood collection device in its first position for drawing blood from a patient.

FIG. 4 is a cross-sectional view of the blood collection device in its retracted position.

DESCRIPTION OF THE PREFERRED EMBODIMENT

Referring to FIGS. 1-4, a syringe, or needle-vacuum tube holder 2 constructed in accordance with the present invention generally comprises an outer, tubular housing 4 having an open end 6 and a radially outwardly extending flange 8 at that end. The housing defines a cylindrical sleeve 10 which extends to another end of the housing that is closed by a transverse end wall 12. A coaxial aperture 14 in the end wall permits the passage therethrough of a conventional needle 16 as is further described below.

A needle-vacuum tube carrier 18 is disposed within the tubular housing and axially movable between first and second positions. The carrier has a tubular section 20 which includes an open end 22 facing in the same direction as open end 6 of housing 4. The other end of the carrier is closed by an end wall 24 which defines a hub 26 having a threaded portion 28 which threadably engages the needle 16 in a conventional manner. If desired, the needle may be otherwise. e.g., permanently fixed to the hub as by integrally molding it or thermally bonding it into the hub (not separately shown). A pre-evacuated collection tube 30 is received within tubular section 20 and includes an elastomeric, sealing end plug 32 which seals the interior of the tube from the exterior. When the carrier is in its distal position (FIG. 3) needle 16 is extended, projects through aperture 14 through transverse end wall 12 and is ready for use after said needle is unshielded. When the carrier is in its proximal position (FIG. 4) the needle is disposed inside housing 4 for safe storage after use until the syringe can be properly disposed of.

To use the blood collection tube holder, and with the carrier in its distal position, a laboratory technician initially attaches needle 16 into the needle carrier, e.g., by threading the needle into hub 26 so that proximal needle end 34 extends into tubular section 20 of carrier 18. A protective collapsible sheathing 36 maintains the needle sterile.

Holding housing 4, the technician pierces a patient's skin with the distal end 38 of the needle to extend it into a vein. While continuing to hold the housing with one hand the technician inserts an unused previously evacuated collection tube 30 into the tubular section 20 of the carrier. As the tube is pushed against the protruding proximal needle end 34, the protective sheathing 36 is first pierced by the proximal needle end which then pierces through evacuated collection tube end plug 32.

Blood now flows from the vein through the needle into the vacuum tube. When sufficient blood has been drawn, the technician separates the vacuum tube from the carrier by axially pulling on the tube with one hand while holding the housing 4 with the other hand. End plug 32 automatically reseals itself after removal of the needle cannula. If additional blood samples are required the technician will repeat the above summarized procedure to attach further, unused evacuated collection tubes to the carrier 18 and thereby draw additional blood samples.

After the last sample has been drawn the now used and contaminated needle is retracted by sliding the carrier relative to the housing axially towards open housing end 6 until the distal needle end 38 is fully retracted within the tubular housing when the carrier is in its proximal position. The housing end wall 12 and the relatively small diameter aperture 14 therein prevent the laboratory technician from accidentally contacting or striking the free end 38 of the now contaminated needle. The spread of infectious diseases through such contact is thereby prevented.

To facilitate the axial movement of carrier 18 within tubular housing 4 and hold it in its two operative positions the housing includes an elongated, typically axially oriented slot 40. An actuator attached to and extending radially from carrier 18 projects through the slot to the exterior of the sleeve. The actuator includes a head or button 44 which is readily grasped by the technician and with which the carrier can be moved between its two operative positions as is described below.

Slot 40 extends from the open housing end 6 to a distal, round opening 46 which is adjacent to housing end wall 12. The opening has a diameter greater than the width of a distal portion 48 of the slot which communicates with it. A proximal opening 50 is axially spaced from the distal opening, is proximate the open end 6 of the tubular housing, and communicates with a proximal portion 52 of the slot which is an extension of the distal slot portion 48. The proximal opening further communicates with a remainder 54 of slot 40 as is clearly illustrated in FIG. 1.

From the foregoing it will be observed that slot 40 extends over a major portion of the length of tubular housing 4 and segments it axially. The housing is constructed of a relatively flexible material, such as an injection molded plastic, so that it can be flexibly spread apart along the slot to increase the width of slot 40 by applying tangentially-opposing, outwardly directed forces to the housing on each side of the slot. Conversely, upon the release of the forces, the housing resiliently returns to its original as-molded position.

For reasons further described below, the proximal opening 50 is a cornered opening, such as a square opening (not illustrated) or a parallelogram-shaped opening (shown in FIGS. 1 and 2) defined by four spaced apart corners 56(a)–(c) interconnected by four, preferably straight edges 58(a)–(c). The edge 58(a) of proximal opening 52 adjacent slot portion 52 is preferably inclined relative to the slot by an angle "A" of less than 90° and, preferably, of about 60°. All other straight edges 58(b)–(d) are correspondingly inclined to define the parallelogram-shaped hole. The transverse dimension of opening 50 equals the length of edge 58(a) and exceeds the width of slot 52 at the point where it meets the proximal opening.

For purposes described more fully below, the width of slot portion 48 where it meets distal opening 46 is slightly greater than the width of proximal opening 52, i.e., slightly greater than the length of straight edge 58(a). Further, the diameter of distal opening 46 is greater than the width of the first slot portion 48.

The actuator 42 of carrier 18 is preferably integrally constructed with carrier 18, e.g., molded therewith, and is defined by a stem 60 which extends from tubular section 20 to actuator head 44. The stem has a base section 62 attached to the tubular section of the carrier and a diameter substantially equal to the diameter of distal opening 46 so that base section can extend into the distal opening. An intermediate portion 64 of the stem extends from the base 62 to head 44. It is shaped complementary to proximal opening 52 in sleeve 10, i.e., in the above-described preferred embodiment of the present invention the intermediate stem portion has the shape of a parallelogram and is dimensioned so that it can be snugly received in the proximal opening of the sleeve.

Further, the tubular section 20 of carrier 18 is constructed of a flexible material, such as injection molded plastic, and it is shaped so that by applying a radially inwardly directed force to actuator head 44 the tubular carrier section can be resiliently deflected inwardly. In a presently preferred embodiment such a resiliently flexible mounting of the actuator is effected by positioning longitudinally extending cutouts 66, 68 on each side of the actuator. The cutouts facilitate the above-described inward deflection of the actuator. If desired, the tubular section 20 of the carrier can be provided with additional openings 68 to increase visibility of the sample as it is being drawn and to reduce its weight and thereby save material costs.

Carrier 18 is initially, usually at the factory, inserted into tubular housing 4 by aligning stem 60 of actuator 42 with slot 40. The slot is spread apart to increase its width sufficiently (usually with appropriate fixtures) to allow the insertion of the carrier into the housing by sliding the actuator 42 along the slot until the stem is aligned with distal opening 46. When the stem base is aligned with the distal opening the resilient force generated by tubular section 20 of the carrier biases the actuator outwardly and the base section 62 into the distal opening. This positions the carrier in its distal or "armed" position. i.e., the position at which carrier hub 26 extends through end wall aperture 14 of the housing. Since the base section 62 has a greater diameter than the width of the adjoining slot portion 48, the carrier cannot be moved axially relative to the tubular housing even when an axial force is applied to it.

The technician now places a fresh needle into the hub and syringe 2 is ready for use by piercing a patient's skin with distal needle end 38 to reach a vein of the patient. Thereafter, one or more evacuated blood collection tubes are inserted into the interior of tubular carrier section 20 and the required blood samples are drawn in the above-described manner.

After the last sample has been drawn and the last evacuated blood collection tube has been removed from carrier 18, the technician withdraws needle 16 from the patient. Immediately thereafter he compresses actuator head 44 radially inwardly until the head engages the exterior of housing 4. This aligns intermediate stem portion 62 with the slot section 48 and since the latter is slightly wider than the former, the carrier can now be moved axially towards open housing end 6 to retract the needle into the interior of the housing. As the actuator is retracted (proximally) rearwardly, that is towards opening housing end 6, the intermediate stem portion 62 engages tapered sides 70 between the relatively wide and narrow slot sections 48 and 52 over the length of which the width of the slot decreases. As the actuator is moved rearwardly tangentially-opposing lateral component forces are generated by the engagement of the intermediate stem portion 64 with the tapered slot sides. This opens the slot by flexibly spreading the housing along the slot to accommodate the stem portion and permit the continued rearward movement of the carrier.

Once the intermediate stem portion 62 reaches the proximal cutout 52 the resiliency of the housing snaps it back into its original, relaxed position. The intermediate stem portion 64 is thereby simultaneously aligned with and locked to the proximal opening 50 without any further manipulation being either necessary or possible on the part of the technician. Once locked, the actuator and therewith the carrier and the needle attached thereto cannot again be moved towards the distal opening. The carrier and the needle are locked in their retracted position because the straight edge 58(a) of the proximal opening cooperates with the corresponding side of the intermediate stem portion and prevents an axially directed force applied to the actuator head from again spreading the slot apart. By angularly inclining edge 58(a) as above described, an undercut is formed. In the arrangement illustrated in FIG. 2 the undercut is at corner 56(a). It forms an anchor which makes it almost impossible to accidentally open the slot even when applying a relatively large axial force to the actuator.

Variations and modifications can be made to the present invention without departing from the scope of the invention. For example, the shape of the proximal opening may be a rectangular or triangular. Further, a spring may be employed to bias the device into its second retracted position or the button may be attached to the cylinder and the parallelogram slot to the needle carrier. It is to be understood that the scope of the invention is limited only by the following claims.

I claim:

1. A blood collection device comprising:
   an outer sleeve and an inner needle carrier for receiving a double-pointed needle;
   said outer sleeve including a longitudinally extending slot having first and second locations;
   said inner needle carrier being mounted within said outer sleeve for axial movement between the first location, at which said needle is adapted to project from said outer sleeve in an exposed position for drawing blood, and the second location, at which said needle is adapted to be fully disposed within said outer sleeve in a retracted position after use;
   said inner needle carrier including an actuator, movable radially and longitudinally relative to the outer sleeve, passing through the slot;
   detent means, at the first location, cooperatively defined by the actuator and the slot in the outer sleeve, for releasably holding said inner needle carrier at the first location for use of the needle;
   locking means, at the second location, cooperatively defined by the actuator and the outer sleeve, for non-releasably locking said inner needle carrier at said second location after the use of the needle; and
   the actuator and the slot configured so the actuator is in first and second radial positions relative to the sleeve when the inner needle carrier is in the first and second locations.

2. The device of claim 1 wherein the first and second locations are axially-aligned.

* * * * *